(12) United States Patent
Glaug et al.

(10) Patent No.: US 9,095,479 B2
(45) Date of Patent: Aug. 4, 2015

(54) DISPOSABLE ABSORBENT PRODUCT WITH COATED ELEMENT AND RELATED METHODS

(75) Inventors: Frank Stephen Glaug, Chester Springs, PA (US); Michael Franklin Kalmon, Ball Ground, GA (US)

(73) Assignee: SCA HYGIENE PRODUCTS AB, Gothenburg (SE)

( * ) Notice: Subject to any disclaimer, the term of this patent is extended or adjusted under 35 U.S.C. 154(b) by 105 days.

(21) Appl. No.: 13/561,513

(22) Filed: Jul. 30, 2012

(65) Prior Publication Data
US 2014/0031776 A1  Jan. 30, 2014

(51) Int. Cl.
*A61F 13/537* (2006.01)
*A61F 13/53* (2006.01)
*A61F 13/534* (2006.01)
*A61F 13/539* (2006.01)

(52) U.S. Cl.
CPC .............. *A61F 13/53* (2013.01); *A61F 13/534* (2013.01); *A61F 13/539* (2013.01); *A61F 2013/5349* (2013.01); *A61F 2013/530481* (2013.01)

(58) Field of Classification Search
CPC .................. A61F 13/15666–13/15691; A61F 2013/53472; A61F 2013/5349; A61F 2013/5315
See application file for complete search history.

(56) References Cited

U.S. PATENT DOCUMENTS

| | | | | |
|---|---|---|---|---|
| 4,402,689 A * | 9/1983 | Baum | | 604/387 |
| 5,260,345 A | 11/1993 | DesMarais et al. | | |
| 5,387,207 A | 2/1995 | Dyer et al. | | |
| 5,458,592 A * | 10/1995 | Abuto et al. | | 604/378 |
| 5,650,222 A | 7/1997 | DesMarais et al. | | |
| 5,785,696 A * | 7/1998 | Inoue et al. | | 604/378 |
| 5,849,805 A | 12/1998 | Dyer | | |
| 6,583,332 B1 | 6/2003 | Werenicz et al. | | |
| 6,646,180 B1 * | 11/2003 | Chmielewski | | 604/368 |
| 7,078,075 B1 | 7/2006 | Werenicz et al. | | |
| 7,855,314 B2 * | 12/2010 | Hanao et al. | | 604/358 |
| 8,581,018 B2 * | 11/2013 | Ito et al. | | 604/359 |
| 2002/0138059 A1 * | 9/2002 | Van Gompel et al. | | 604/385.22 |

(Continued)

FOREIGN PATENT DOCUMENTS

EP   1 870 067 A1   12/2007

OTHER PUBLICATIONS

"Block Copolymer", Eastman (http://www.eastman.com/Markets/Tackifier_Center/Pages/Block_Copolymer.aspx), printed Mar. 12, 2015.*

(Continued)

*Primary Examiner* — Susan Su
(74) *Attorney, Agent, or Firm* — Buchanan Ingersoll & Rooney PC

(57) ABSTRACT

A disposable absorbent product includes a topsheet defining an interior face of the disposable absorbent product configured to face a wearer thereof during use. A backsheet overlays the topsheet, with the backsheet defining an exterior face of the disposable absorbent product configured to face away from the wearer during use. An absorbent core is disposed between the topsheet and the backsheet for storing fluid secreted by the wearer of the disposable absorbent product. The absorbent core includes at least one absorbent structure and a wrapping element that envelops the at least one absorbent structure. The wrapping element has a main substrate layer and an adhesive coating layer thereon that is substantially adhered to the substrate layer and which defines an impermeable film layer on the substrate.

18 Claims, 3 Drawing Sheets

(56) References Cited

U.S. PATENT DOCUMENTS

| | | | |
|---|---|---|---|
| 2003/0208172 A1* | 11/2003 | Werenicz et al. | 604/367 |
| 2003/0208176 A1* | 11/2003 | Waksmundzki et al. | 604/378 |
| 2004/0127871 A1* | 7/2004 | Odorzynski et al. | 604/378 |
| 2004/0158212 A1* | 8/2004 | Ponomarenko et al. | 604/367 |
| 2006/0068113 A1* | 3/2006 | Aoyama et al. | 427/356 |
| 2006/0069368 A1* | 3/2006 | Van Himbergen et al. | 604/378 |
| 2006/0135932 A1* | 6/2006 | Abuto et al. | 604/385.22 |
| 2006/0253092 A1* | 11/2006 | Ponomarenko et al. | 604/360 |
| 2007/0049892 A1* | 3/2007 | Lord et al. | 604/385.16 |
| 2007/0276349 A1 | 11/2007 | Mori et al. | |
| 2008/0118689 A1* | 5/2008 | Mehta et al. | 428/35.7 |
| 2009/0004435 A1* | 1/2009 | Hanao et al. | 428/156 |
| 2010/0249737 A1* | 9/2010 | Ito et al. | 604/367 |
| 2010/0280472 A1* | 11/2010 | Takeuchi et al. | 604/367 |
| 2010/0312206 A1* | 12/2010 | Fujioka | 604/365 |
| 2011/0178489 A1* | 7/2011 | Baba et al. | 604/385.3 |
| 2012/0296294 A1* | 11/2012 | Hashimoto et al. | 604/367 |
| 2013/0165882 A1* | 6/2013 | Kawakami et al. | 604/374 |
| 2014/0171894 A1* | 6/2014 | Detani et al. | 604/374 |

OTHER PUBLICATIONS

"Hydrogenated styrenic block copolymer offers benefits for PSAs", ASI Adhesives & Sealants Industry, Mar. 20, 2003.*

Notification of Transmittal of the International Search Report (Forms PCT/ISA/220 and PCT/ISA/210) and the Written Opinion of the International Searching Authority (Form PCT/ISA/237) issued in the corresponding International Application No. PCT/EP2013/060944 dated Aug. 5, 2013. (9 pages).

Notification Concerning Transmittal of International Preliminary Report on Patentability (Forms PCT/IB/326 and PCT/IB/373) and the Written Opinion of the International Searching Authority (Form PCT/ISA/237) issued on Feb. 12, 2015 by the International Bureau of WIPO in corresponding International Application No. PCT/EP12012/055554. (7 pages).

* cited by examiner ical FIELD

DISPOSABLE ABSORBENT PRODUCT WITH COATED ELEMENT AND RELATED METHODS

TECHNICAL FIELD

The present invention is generally related to absorbent products and, more particularly, to disposable absorbent products that are worn by humans for the containment and absorption of fluid bodily secretions.

BACKGROUND

Disposable absorbent products for absorption of bodily fluids are available in different types, designs, and dimensions. For example, training pants, baby diapers, adult diapers, and incontinence guards are products designed for the containment of urine and excrement. There are other types of disposable absorbent articles, such as feminine hygiene products (e.g., heavy and light incontinence pads, pantiliners) that are designed to contain and absorb urine and/or menses secreted by female wearers. Known products of this type typically include a topsheet facing the body of the wearer, a backsheet facing the garment worn by the wearer, and an absorbent core sandwiched between the topsheet and backsheet.

The absorbent core in products of the type described above include a main absorbent structure that is configured to distribute and store fluids secreted by the wearer, as well as other components such as acquisition components and the like. The main absorbent structure in conventional products has granular storage components, such as Super Absorbent Particles ("SAP"), that gel-up when placed in contact with urine or other fluids secreted by the wearer. Prior to gelling-up, however, these granular components may be hard, which may cause discomfort to the wearer, or even poke through the surrounding layers of material.

In order to minimize the problems associated with the hard granular components, manufacturers of disposable absorbent products of this type often wrap the main absorbent structure of the absorbent core with a thin layer of paper, which allows passage of fluid therethrough while preventing exposure of the granular components through the topsheet. Wrapping with a thin layer of paper also maintains the granular components in the intended target area within the disposable absorbent product, which enhances containment of the secreted fluids.

But wrapped-core designs of the type described above often require an additional barrier layer of material, such as an impermeable polyethylene-based layer, located between the wrapped core and the backsheet of the product. This is to prevent fluid stored in the core from reaching the backsheet, which may be undesirable. The presence of the additional barrier layer increases the cost and complexity in the manufacturing of the disposable absorbent product.

Accordingly, it is desirable to provide disposable absorbent products that address these and other shortcomings of conventional disposable absorbent products.

SUMMARY

In one embodiment, a disposable absorbent product is provided that includes a topsheet defining an interior face of the disposable absorbent product configured to face a wearer thereof during use. A backsheet overlays the topsheet, with the backsheet defining an exterior face of the disposable absorbent product configured to face away from the wearer during use. An absorbent core is disposed between the topsheet and the backsheet for storing fluid secreted by the wearer of the disposable absorbent product. The absorbent core includes at least one absorbent structure and a wrapping element that envelops the at least one absorbent structure. The wrapping element has a main substrate layer and an adhesive coating layer thereon that is substantially adhered to the substrate layer and which defines an impermeable film layer on the substrate.

In specific embodiments, the main substrate layer completely envelops the at least one absorbent structure, thereby defining a wrapping element with four walls surrounding the at least one absorbent structure. The four walls include two side walls, a top wall adjacent the topsheet, and a bottom wall adjacent the backsheet. Additionally, the disposable absorbent product may be free of any additional impermeable film layers disposed between the bottom wall and the backsheet. The at least one absorbent structure comprises, in specific embodiments, first and second absorbent structures. The first and second absorbent structures may be both primarily configured for storage of fluid secreted by the wearer.

The top wall may be substantially free of the adhesive coating layer. In other embodiments, the main substrate layer only partially envelops the at least one absorbent structure, thereby defining a wrapping element with three walls surrounding the at least one absorbent structure. The three walls include two side walls, as well as a bottom wall adjacent the backsheet. The wrapping element in those embodiments is substantially free of a wall opposite the bottom wall, adjacent the topsheet. The main substrate layer and the adhesive coating layer have, in some embodiments, respective pairs of lateral ends, with the lateral ends of the main substrate layer generally coinciding with the lateral ends of the adhesive coating.

In embodiments having first and second absorbent structures, the first absorbent structure may be primarily configured for acquisition and distribution of fluid secreted by the wearer, while the second absorbent structure may be primarily configured for storage of fluid secreted by the wearer. The first absorbent structure is, in specific embodiments, at least substantially free of granular components. Additionally or alternatively, the first absorbent structure may be at least substantially free of super absorbent material.

The adhesive coating layer is formed, in some embodiments, from a hot-melt adhesive. Additionally or alternatively, the adhesive coating layer may be tacky at room temperature. The adhesive coating layer may have a basis weight of less than about 20 g/m². In specific embodiments, the adhesive coating layer has a basis weight no greater than about 10 g/m². For example, the adhesive coating layer may have a basis weight of at least about 5 g/m² but less than about 10 g/m². Additionally or alternatively, the backsheet is made of a nonwoven material.

In another embodiment, a disposable absorbent product is provided having a hydrophilic topsheet defining an interior face of the disposable absorbent product configured to face a wearer thereof during use. The product also has a nonwoven backsheet overlaying the topsheet, with the backsheet defining an exterior face of the disposable absorbent product configured to face away from the wearer during use. An absorbent core is disposed between the topsheet and the backsheet for storing fluid secreted by the wearer of the disposable absorbent product. The absorbent core includes at least one absorbent structure and a wrapping element enveloping the at least one absorbent structure. The wrapping element has a main substrate layer and an adhesive coating layer thereon, with the adhesive coating layer being formed from a hot-melt adhesive, being tacky at room temperature, and having a basis weight of less than about 20 g/m². The disposable absorbent product in that embodiment is free of any additional impermeable barriers disposed between the bottom wall and the backsheet.

In yet another embodiment, a method is provided for forming an absorbent core for use in a disposable absorbent product, in which the absorbent core is disposed between a backsheet and a topsheet overlaying one another. The method includes obtaining an absorbent structure primarily configured for storage of fluid secreted by a wearer of the disposable absorbent product, and obtaining a main substrate layer. A coat of adhesive material is applied onto the main substrate layer to thereby define an impermeable film layer on the main substrate layer, and the absorbent structure is enveloped with the coated main substrate layer to thereby define the absorbent core. The method may additionally include dispensing the adhesive material from a non-contact slot coating device and onto the main substrate layer.

BRIEF DESCRIPTION OF THE DRAWINGS

The objectives and features of the invention will become more readily apparent from the following detailed description taken in conjunction with the accompanying drawings in which.

DETAILED DESCRIPTION

To the extent that any meaning or definition of a term in this written document conflicts with any meaning or definition of the term in a document incorporated by reference, the meaning or definition assigned to the term in this written document shall govern. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
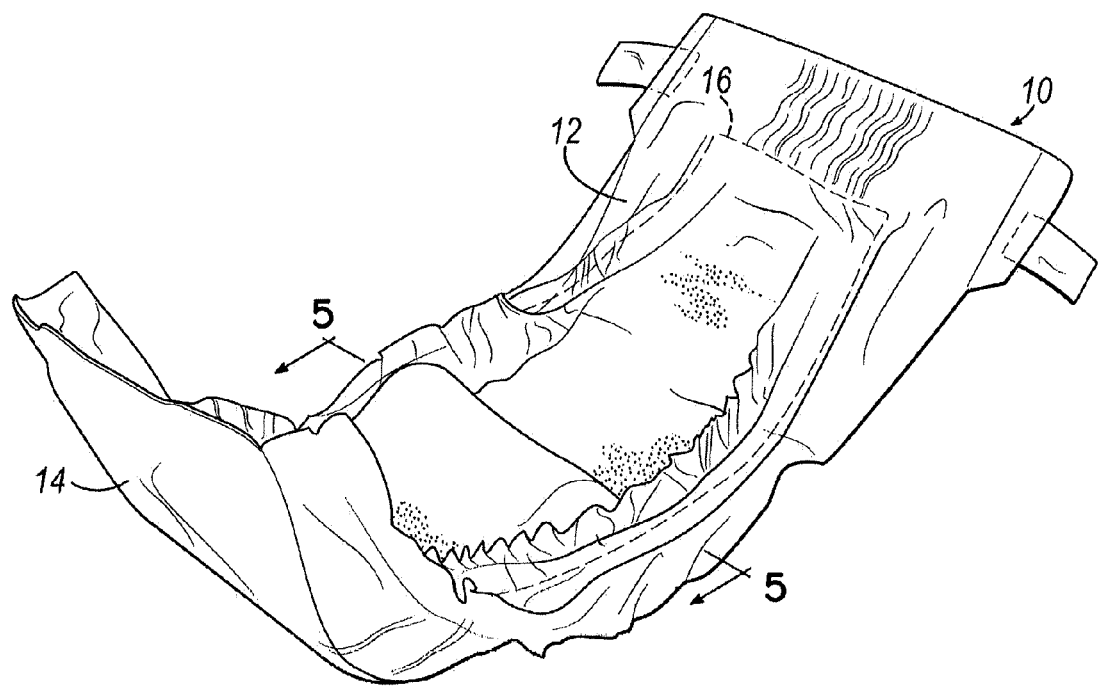
FIG. 1 is a perspective view of a disposable absorbent product in accordance with one embodiment of the invention.
Figure 2:
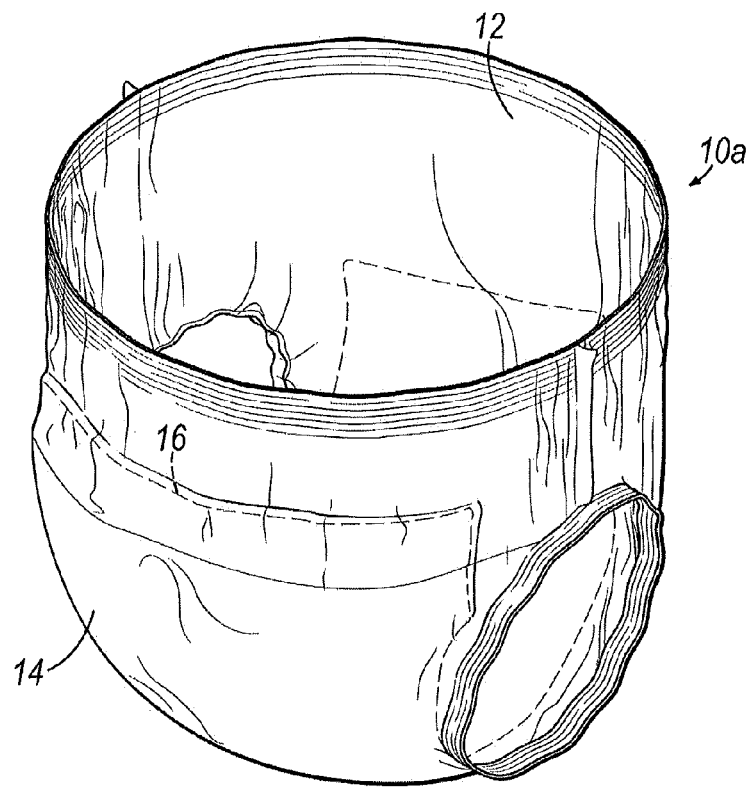
FIG. 2 is a perspective view of a disposable absorbent product in accordance with another embodiment of the invention.

With reference to the figures, and more particularly to FIGS. 1 and 2, an exemplary disposable absorbent product in the form of a diaper 10 is illustrated. Diaper 10 could be a baby diaper or an adult diaper ("brief") or a belted undergarment, for example. While these and other figures refer to a disposable absorbent product in the form of a diaper, it is contemplated that one or more of the features described and/or illustrated herein are applicable to other types of disposable absorbent products, and these are therefore not limited to the exemplary diapers described herein. For example, and without limitation, one or more of the various features described herein may be also used in closed pant-type products such as the exemplary training pant 10a shown in FIG. 2.

Yet other products contemplated herein include but are not limited to adult-size disposable pads, feminine catamenial pads, or male or female light-incontinence, medium-incontinence, or heavy-incontinence pads.

For ease of understanding, exemplary details are described with reference to "diaper 10," which is the embodiment illustrated in FIG. 1, though it is understood that the features and functions described with respect to that embodiment are similarly applicable to the embodiment of FIG. 2 or to any other embodiments of the types generally described herein. Diaper 10 includes a topsheet 12 and a backsheet 14 disposed opposite the topsheet 12, such that the topsheet 12 and backsheet 14 are in an overlaying relationship with one another. In use, the topsheet 12 at least partially defines an interior face of the diaper 10 that faces the body of the wearer. The backsheet 14, by contrast, faces away from the body of the wearer and at least partially defines an exterior face of the diaper 10. The topsheet 12 is made of a permeable, hydrophilic material such as a hydrophilic nonwoven, and may be in the form of a single, continuous layer across the length and/or width of the diaper 10, or may alternatively be in the form of two or more layers of the same material or of materials different from one another that jointly, rather than individually, span the length and/or width of the diaper 10.

The backsheet 14 includes an impermeable, hydrophobic material such as a hydrophobic spunbond nonwoven or a laminate made of one or more layers of nonwoven materials and one or more layers of an impermeable polypropylene or polyethylene film. Backsheet 14 may be in the form of a single, continuous layer across the length and/or width of the diaper 10, or may alternatively be in the form of two or more layers of the same material or of materials different from one another that jointly, rather than individually, span the length and/or width of the diaper 10.

Figure 3:
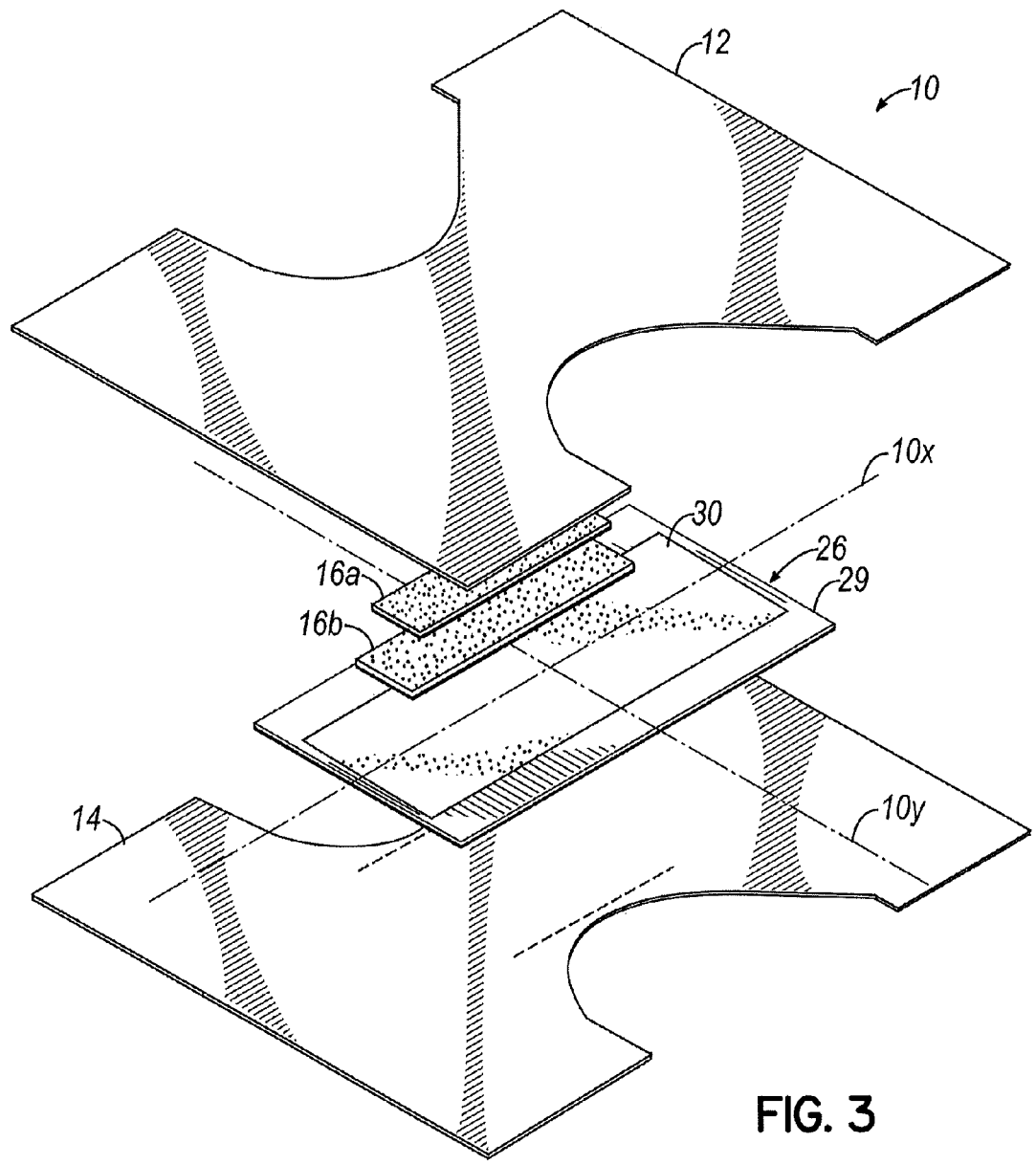
FIG. 3 is a disassembled, schematic perspective view of the disposable absorbent product of FIG. 1 or FIG. 2.
Figure 4:
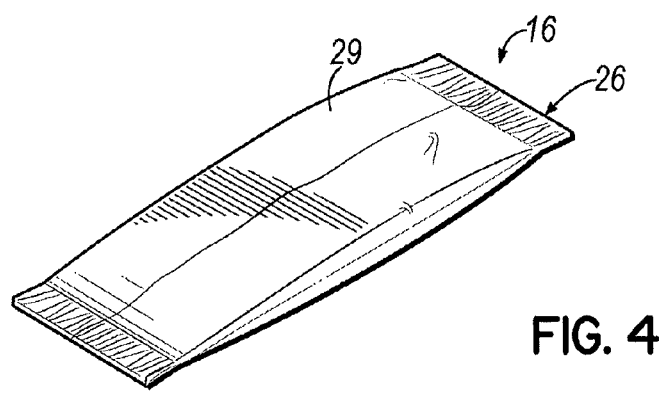
FIG. 4 is a perspective view of an absorbent core of the product of FIG. 3.

With continued reference to FIGS. 1-2, and further referring to FIGS. 3-4, the diaper 10 also includes an absorbent core 16 that is disposed between the topsheet 12 and the backsheet 14, and which is configured to absorb and retain body fluids, such as urine and/or menses, secreted by the wearer. The core 16 may have a single main absorbent structure or may instead have, as in the exemplary embodiment of FIG. 3, first and second absorbent structures 16a, 16b, each made up of fluff pulp or a combination of fluff pulp or some other natural or synthetic fluid management material, and a fluid storage material such as SAP or some other natural or synthetic fluid storage material. More specifically in the embodiment of FIG. 3, the core 16 includes an upper absorbent structure 16a that is supported by a larger bottom absorbent structure 16b.

Those of ordinary skill in the art will readily appreciate that the absorbent structures 16a, 16b may have relative dimensions and shapes that are different from those shown in FIG. 3, and still fall within the scope of the present disclosure. Each of the absorbent structures 16a, 16b in that embodiment is primarily configured for storage of fluid, such as urine, that is secreted by the wearer of the disposable absorbent product. Alternatively, one of the absorbent structures 16a, 16b may be primarily configured for fluid storage, while the other of the absorbent structures 16a, 16b is primarily configured for rapid acquisition and distribution of fluid toward other components of the core 16 that are primarily configured for fluid storage. For example, and without limitation, the upper absorbent structure 16a may be an airlaid-based material, while the lower absorbent structure 16b may be have a mixture of fluff pulp and SAP or some other granular fluid storage component. Alternatively, the bottom (i.e., second) absorbent structure 16b may also be an airlaid-based material.

Exemplary airlaid-based materials of the type discussed above are known as "VH600.101.B6001" and "VH460.103.B6001," both commercially available from Glatfelter Falkenhagen GmbH, of Falkenhagen, Germany. Other exemplary materials for upper absorbent structure 16a are foam-based materials such as those known as High Internal Phase Emulsion (HIPE) foams, of the types described, for example, in U.S. Pat. Nos. 5,387,207; 5,260,345, 5,650,222; and 5,849,805, the respective entire disclosures of which are hereby expressly incorporated by reference herein.

Core 16, as well as the diaper 10 of which core 16 forms part, extend along a longitudinal axis 10x (longitudinal dimension), and along a transverse axis 10y (width dimension) orthogonal to the longitudinal axis 10x. The core 16 could be generally rectangular, or have an hourglass shape, or have any other regular or irregular, symmetrical or asymmetrical shape, and still fall within the scope of the present disclosure.

With continued reference to FIGS. 1-4, the core 16 of the illustrated embodiment includes a thin wrapping element 26 of permeable, hydrophilic material such as paper or a hydrophilic nonwoven. Wrapping element 26 envelops the absorbent structures 16a, 16b so as to prevent exposure of granular components of the core 16, such as granular SAP, to surrounding layers. Further, wrapping element 26 maintains the different components of absorbent structures 16a, 16b together, which enhances the dry and wet integrity of core 16, thereby enhancing fluid containment.

Figure 5:
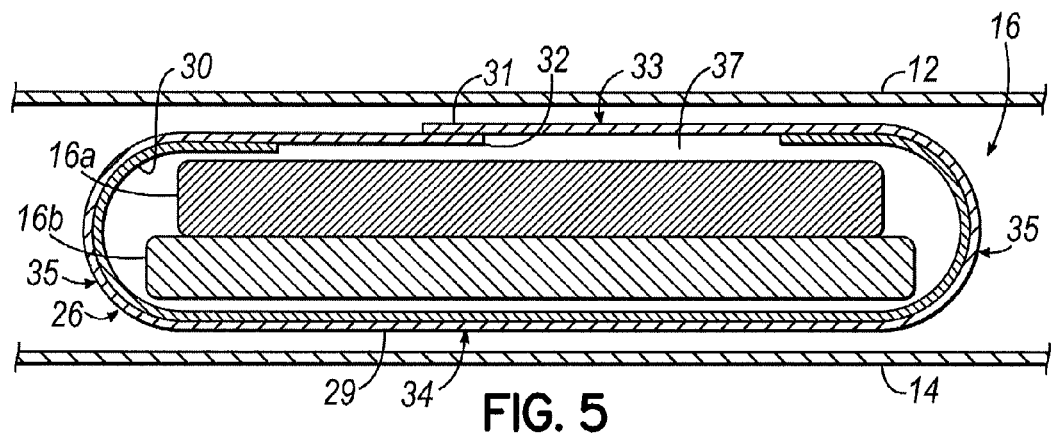
FIG. 5 is a cross-sectional view taken generally along line 5-5 of FIG. 1.

With continued reference to FIGS. 1-4, and further referring to FIG. 5, wrapping element 26 includes a main substrate layer 29 and a continuous coating 30 of a film barrier adhesive material formed on the interior face of main substrate layer 29. More specifically, wrapping element 26 includes a coating 30 of an adhesive material that is also impermeable, with the impermeability being such that it prevents the transfer of fluid secreted by the wearer from the absorbent structures 16a, 16b onto the backsheet 14 of diaper 10. The impermeability of coating 30 makes it unnecessary to provide an additional barrier layer adjacent the backsheet 14, and thereby simplifies the manufacturing of diaper 10. Further, the adhesive functionality of coating 30 also enhances the dry and wet integrity of core 16, by virtue of the engagement of SAP, fluff pulp and/or any other components of core 16 by the adhesive coating 30, which fixes those components in place.

The coating 30 has suitably chosen levels of tackiness and impermeability. For example, and without limitation, coating 30 may be a hot-melt adhesive that is generally tacky at room temperature i.e., between about 18° C. and about 23° C. Similarly, coating 30 may be substantially impermeable be virtue of being substantially or completely free of pin-holes at basis weights that are less than about 20 g/m². In specific embodiments, the coating 30 is substantially or completely free of pin-holes at basis weights between about 10 g/m² and about 20 g/m², or even at basis weights that are less than about 10 g/m², such as basis weights between about 5 g/m² and about 10 g/m². Exemplary materials for coating 30 are materials known by the names Lunatack® NW 1192 ZP®, Lunatack® D-8370, Lunatack® D-9105, and Lunatack® D-3964, all of which are hot-melt adhesives commercially available from the H.B. Fuller Company, of St. Paul, Minn., United States of America. Exemplary hot-melt adhesives suitable for coating 30 include at least one thermoplastic polymer (up to about 40% by weight), at least one plasticizer (up to about 40% by weight), and at least one tackifying resin (up to about 70% by weight).

These non-limiting examples of hot-melt adhesives may have a low melting point temperature, such as in the range of about 60° C. to about 110° C. These relatively low melting point temperatures facilitate application of coating 30 to materials such as paper and thin nonwoven substrates that are susceptible to damage when exposed to high temperatures. In addition, the rheological properties of some of these hot-melt adhesives facilitate the application of a continuous, moisture and/or fluid impermeable coating at low basis weights. More specifically, hot-melt adhesives are contemplated for coating 30 in which the complex viscosity at high shear rates (1,000 rad/sec) is less than about 500 poise and the complex viscosity at low shear rates (<1 rad/sec) is between about 100 and about 1,000 poise. Thermoplastic-containing hot-melt adhesives of this type thus exhibit Newtonian regions at low shear rates and shear thinning at high shear rates. These hot-melt adhesives substantially adhere to the surface of main substrate layer 29 without deeply penetrating into the main substrate layer 29, forming a fluid (i.e., liquid) and/or moisture impermeable film barrier layer on main substrate layer 29.

Coating 30 is applied to the main substrate layer 29 of wrapping element 26 in a suitably chosen thickness, such as one corresponding to a basis weight anywhere in the range between about 5 g/m² and about 20 g/m², or any other basis weight. In a specific embodiment, the basis weight is about 15 g/m². Application of the coating 30 onto main substrate layer 29 is carried out through a suitably chosen process for applying a coating in liquid form, such as a hot-melt adhesive, so as to define an impermeable film coating that is substantially adhered to the main substrate layer 29. For example, and without limitation, coating 30 may be applied onto main substrate layer 29 with a slot coater that dispenses the coating material but which does not contact the main substrate layer 29. This results in a substantially uniform, continuous coating of the coating material (e.g., hot-melt adhesive) onto the main substrate layer 29. An exemplary process suitable to apply the coating 30 is described in U.S. Pat. No. 7,078,075, the entire contents of which are hereby expressly incorporated by reference herein.

The main substrate layer 29 is also suitably chosen and may, for example, be in the form of a layer of tissue-type paper, having a basis weight of about 18 g/m². The main substrate layer 29 may instead be in the form of a layer of a nonwoven material and still fall within the scope of the present disclosure. An exemplary material for main substrate layer 29 is known as a tissue of "Grade 3253," commercially available from the Cellu Tissue Holdings, Inc. of East Hartford, Conn., United States of America.

With particular reference to FIG. 5, the lateral extent of main substrate layer 29 and of coating 30 are chosen so as not to interfere with the flow of fluid into the core 16. Specifically, in the embodiment illustrated in that figure, the lateral extent of main substrate layer 29 is such that same completely encases the absorbent structures 16a, 16b, with the lateral ends 31, 32 of main substrate layer 29 overlapping one another, as illustrated at the top of FIG. 5. As used herein, the term "lateral extent" refers to the extent, in the width direction of diaper 10, to which a particular folded component (e.g., layer) extends if that component were to be laid flat rather than in its folded configuration. The wrapping element 26 thus defines top and bottom walls 33, 34 and side walls 35 that contain the absorbent structures 16a, 16b therein. The coating 30 only extends partially in the width direction of diaper 10. More specifically, the coating 30 in the illustrated embodiment laterally extends so as to cover the bottom wall 34 and side walls 35, while leaving the top wall substantially free of coating 30. This design allows for the ready passage of fluid received through the topsheet 12 into the interior 37 of core 16, while preventing fluid from escaping through the bottom wall 34 or the side walls 35. Further, the adhesive properties of coating 30 engage portions of the absorbent structures 16a, 16b therein, which enhances integrity of core 16, thereby enhancing product appearance and fluid containment.

Figure 6:
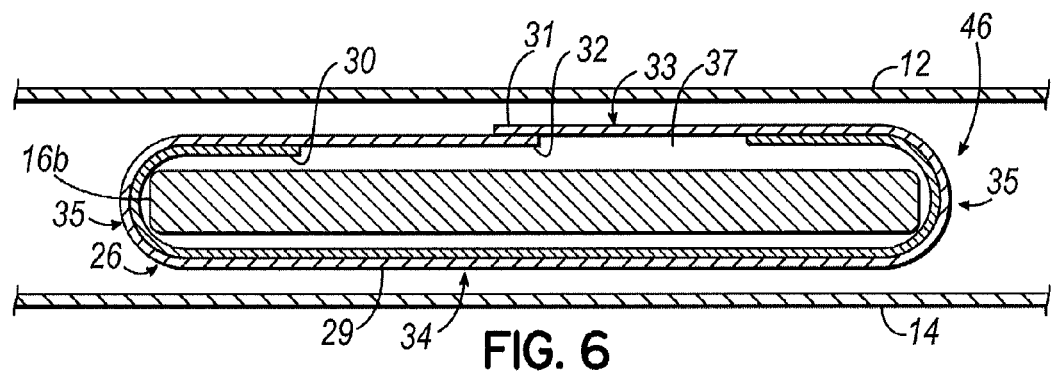
FIG. 6 is a cross-sectional view similar to FIG. 5, in accordance with another embodiment of the invention.

With reference to FIG. 6, another embodiment is illustrated of a core 46, similar in most respects to the core 16 of the preceding figures, but having a single absorbent structure 16b, rather than two such structures. In FIG. 6, like reference numerals refer to similar features in the preceding figures, the description of which may be referred-to for an understanding of the structure and functional aspects of the embodiment in this figure as well.

Figure 7:
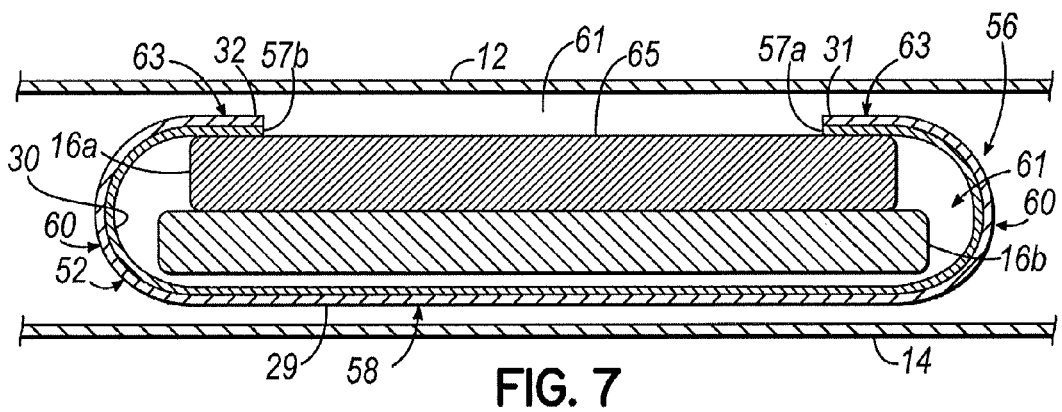
FIG. 7 is a cross-sectional view similar to FIGS. 5 and 6, in accordance with yet another embodiment of the invention.

Referring now to FIG. 7, yet another embodiment is illustrated of a core 56. Like reference numerals in that figure refer to similar features in the preceding figures, the description of which may be referred-to for an understanding of the structure and functional aspects of the embodiment in this figure as well. In the embodiment illustrated in FIG. 7, the lateral extent of the main substrate layer 29 and of coating 30 are the same or at least substantially the same, such that the lateral ends 31, 32 of main substrate layer 29 generally coincide with the lateral ends 57a, 57b of the coating 30. Notably in this embodiment, the lateral extents of the main substrate layer 29 and coating 30 define an encasement for core 56 that; unlike the embodiments of FIGS. 5 and 6, is substantially free of a top wall. More specifically, core 56 has a wrapping element 52 that defines a bottom wall 58 and side walls 60, all of which include portions of the main substrate layer 29 and coating 30. In this embodiment, the flow of fluid through the topsheet 12 and into the interior 61 of core 56 is completely unrestricted, while the presence of coating 30 in the bottom and side walls 58, 60 prevents the flow of fluid through those walls.

Still referring to the embodiment of FIG. 7, the adhesive properties of coating 30 allow the lateral end portions 63 of wrapping element 52 to adhere to the top surface 65 (i.e., adjacent topsheet 12) of the upper absorbent structure 16a, as illustrated in the figure. In specific embodiments, the upper absorbent structure 16a is designed to contain no SAP or any other type of granular components, which therefore obviates the need for complete encasing of the upper and lower absorbent structures 16a, 16b. In that regard, and as explained above, the upper absorbent structure 16a may be in the form of a layer of a material predominantly intended for rapid acquisition and/or distribution of fluid, such as a SAP-free airlaid-based acquisition layer, for example, which is at least substantially, if not completely, free of SAP. Alternatively, in another non-limiting example, the upper absorbent structure 16a may have a zoned distribution of SAP or other granular materials, such that any portion of the top surface 65 that is exposed to the topsheet 12 is at least substantially, if not completely, free granular components. For example, in the illustrated embodiment, the exposed portion of top surface 65 may be completely free of granular components, while the unexposed portions i.e., those portions directly under the end portions 63 of wrapping element 52, contain granular components.

Referring generally to the embodiments of FIGS. 1-7, the integration of an impermeable film barrier layer in the form of a liquid coating 30 with the main substrate layer 29 of wrapping element 26, 52 is advantageous in several different aspects. First, this integration provides liquid and/or moisture impermeability to the main wrapping element 26, 52, without the crackling that would arise, for example, if the main substrate layer 29 was instead bonded with a solid layer of impermeable film material subsequent to forming of the film material. Crackling in diapers and other disposable absorbent products is known to be undesirable because it may lead to the awareness by the wearer and/or by those around him/her, that a disposable product is being worn by the wearer. In addition, the complete integration of the film barrier layer with main substrate layer 29 makes the film barrier layer less susceptible to cracking of that material, thereby contributing to enhanced core integrity during use of the product. Avoiding the formation of cracks in a film is also advantageous because film cracks have been observed to define channels that increase the likelihood of leakage of fluids (e.g., urine) in disposable products. Core integrity could be further enhanced by using a liquid coating 30 of an adhesive material having elastomeric properties, due to the elasticity of the resulting film barrier layer on the main substrate layer 29.

Another advantage is that the application of a coated impermeable film barrier provides flexibility to manufacturers to easily apply, control, and adjust the level and location of impermeable zones to the wrapping element 26, 52. More specifically, the flow of the liquid form of coating 30 can be easily controlled and adjusted during application, as is typically the case, for example, with hot-melt adhesive dispensing. This facilitates adjustment of the desired level of impermeability, which may depend, for example, on the type or thickness of the material used for the main substrate layer 29. This also facilitates easy adjustment of the length and/or width dimensions of the coating 30. Further, this integration provides a method for applying an impermeable film layer to the wrapping element 26, 52 without the need to introduce additional, complex processes and equipment required, for example, to bond a solid layer of film barrier material to the solid main substrate layer 29. Yet another advantage is provided by the adhesive nature of some embodiments of the coating 30, which permits wrapping element 26, 52 to hold the components making up core 16, 46, 56 in place.

From the above disclosure of the general principles of the present invention and the preceding detailed description of exemplary embodiments, those skilled in the art will readily comprehend the various modifications to which this invention is susceptible. Accordingly, this invention is intended to be limited only by the scope of the following claims and equivalents thereof.

What is claimed is:

1. A disposable absorbent product comprising:
   a topsheet defining an interior face of the disposable absorbent product configured to face a wearer thereof during use;
   a backsheet overlaying said topsheet, said backsheet defining an exterior face of the disposable absorbent product configured to face away from the wearer during use; and
   an absorbent core disposed between said topsheet and said backsheet for storing fluid secreted by the wearer of the disposable absorbent product, said absorbent core including at least one absorbent structure and a wrapping element enveloping said at least one absorbent structure, said wrapping element having a main substrate layer and an adhesive coating layer thereon substantially adhered to said main substrate layer and defining an impermeable film layer on said main substrate layer;
   wherein said main substrate layer only partially envelops said at least one absorbent structure, thereby defining a wrapping element with three walls surrounding said at least one absorbent structure, said three walls including two side walls, and a bottom wall adjacent said backsheet, said wrapping element being substantially free of a wall opposite said bottom wall adjacent said topsheet;
   wherein said adhesive coating layer adheres to a top surface of the at least one absorbent structure.

2. The disposable absorbent product of claim 1, wherein said disposable absorbent product is free of any additional impermeable film layers disposed between said bottom wall and said backsheet.

3. The disposable absorbent product of claim 1, wherein said at least one absorbent structure comprises first and second absorbent structures.

4. The disposable absorbent product of claim 3, wherein said first and second absorbent structures are both primarily configured for storage of fluid secreted by the wearer.

5. The disposable absorbent product of claim 1, wherein said main substrate layer and said adhesive coating layer have respective pairs of lateral ends, said lateral ends of said main substrate layer generally coinciding with said lateral ends of said adhesive coating layer.

6. The disposable absorbent product of claim 1, wherein said at least one absorbent structure comprises first and second absorbent structures, said first absorbent structure being primarily configured for acquisition and distribution of fluid secreted by the wearer and said second absorbent structure being primarily configured for storage of fluid secreted by the wearer.

7. The disposable absorbent product of claim 6, wherein said first absorbent structure is substantially free of granular components.

8. The disposable absorbent product of claim 7, wherein said first absorbent structure is substantially free of super absorbent material.

9. The disposable absorbent product of claim 1, wherein said adhesive coating layer is formed from a hot-melt adhesive.

10. The disposable absorbent product of claim 1, wherein said adhesive coating layer is tacky at room temperature.

11. The disposable absorbent product of claim 1, wherein said adhesive coating layer has a basis weight of less than about 20 $g/m^2$.

12. The disposable absorbent product of claim 11, wherein said adhesive coating layer has a basis weight no greater than about 10 $g/m^2$.

13. The disposable absorbent product of claim 12, wherein said adhesive coating layer has a basis weight of at least about 5 $g/m^2$ but less than about 10 $g/m^2$.

14. The disposable absorbent product of claim 1, wherein said backsheet is made of a nonwoven material.

15. The disposable absorbent product of claim 1, wherein the impermeable film layer extends continuously from one side wall, along the bottom wall and to an opposite side wall.

16. The disposable absorbent product of claim 1, wherein the adhesive coating layer includes a plasticizer.

17. The disposable absorbent product of claim 1, wherein the wrapping element directly contacts the at least one absorbent structure.

18. A disposable absorbent product comprising:
    a hydrophilic topsheet defining an interior surface of the disposable absorbent product configured to face a wearer during use; and
    a nonwoven backsheet overlaying a said topsheet, said backsheet defining an exterior face of the disposable absorbent product configured to face away from the wearer during use; and
    an absorbent core disposed between said topsheet and said backsheet for storing fluid secreted by the wearer of the disposable absorbent product, wherein:
    said absorbent core includes at least one absorbent structure and a wrapping element enveloping said at least one absorbent structure, said wrapping element having a main substrate layer and an adhesive coating layer thereon,
    said adhesive coating layer is formed from a hot-melt adhesive, is tacky at room temperature, and has a basis weight of less than about 20 $g/m^2$, and
    the disposable absorbent product is free of any impermeable barriers disposed between said bottom wall and said exterior face of the disposable absorbent product;
    wherein said main substrate layer only partially envelops said at least one absorbent structure, thereby defining a wrapping element with three walls surrounding said at least one absorbent structure, said three walls including two side walls, and a bottom wall adjacent said backsheet, said wrapping element being substantially free of a wall opposite said bottom wall adjacent said topsheet;
    wherein said adhesive coating layer adheres to a top surface of the at least one absorbent structure.

* * * * *